United States Patent [19]

Sakyu et al.

[11] Patent Number: 6,111,150
[45] Date of Patent: *Aug. 29, 2000

[54] METHOD FOR PRODUCING 1,1,1,3,3,-PENTAFLUOROPROPANE

[75] Inventors: Fuyuhiko Sakyu, Miyoshi; Yasuo Hibino, Shiki; Satoshi Yoshikawa, Moroyama; Ryouichi Tamai, Kamifukuoka; Yoshihiko Gotoh, Miyoshi, all of Japan

[73] Assignee: Central Glass Company, Limited, Ube, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/764,496

[22] Filed: Dec. 12, 1996

[30] Foreign Application Priority Data

Jun. 20, 1996 [JP] Japan ..................... 8-159998
Jun. 20, 1996 [JP] Japan ..................... 8-159999
Jul. 1, 1996 [JP] Japan ..................... 8-171097

[51] Int. Cl.$^7$ ................................. C07C 17/08
[52] U.S. Cl. .................. 570/167; 570/166; 570/168
[58] Field of Search .................. 570/166, 167, 570/168

[56] References Cited

U.S. PATENT DOCUMENTS

| | | | |
|---|---|---|---|
| 2,787,646 | 4/1957 | Haszaldine . | |
| 2,830,100 | 4/1958 | Swamer .................... | 570/167 |
| 2,924,036 | 6/1960 | Smith et al. . | |
| 4,374,289 | 2/1983 | Puy et al. ................ | 570/188 |
| 5,015,791 | 5/1991 | Rao ........................ | 570/188 |

FOREIGN PATENT DOCUMENTS

| | | | |
|---|---|---|---|
| 675615 | 12/1963 | Canada ................ | 570/168 |
| 6-256235 | 9/1994 | Japan . | |
| 8-73385 | 3/1996 | Japan . | |
| 8-104655 | 4/1996 | Japan . | |
| WO96/01797 | 1/1996 | WIPO . | |

OTHER PUBLICATIONS

R. N. Haszeldine et al., "The Addition of Free Radicals to Unsaturated Systems. Part II. Radical Addition to Olefins of the Type R·CH:CH$_2$," *J. Chem. Soc.* 1953, 1199–1206.

A. L. Henne et al., "The Preparation and Directed Chlorination of 1,1,1-Trifluoropropane," *J. Am. Chem. Soc.*, May, 1942, vol. 64, pp. 1157–1159.

R.N. Haszeldine, "Reactions of Fluorocarbons Radicals. Part VII. Addition to Trifluoromethyl–substituted Acetylenes," *J. Chem. Soc.*, 1952, pp. 3490–3498.

R. N. Haszeldine, "Reactions of Fluorocarbon Radicals. Part V. Alternative Syntheses for Trifluoromethylacetylene (3:3:3–Trifluoropropyne), and the Influence of Polyfluoro-groups on Adjacent Hydrogen and Halogen Atoms," *J. Chem. Soc.*, 1951, pp. 2495–2504.

English translation of Izvestiya Akademii Nauk SSSR, Otdelenie Khimicheskikh Nauk, No. 8, pp. 1412–1418, Aug., 1960.

M. Katora et al., React.Kinet.Catal.Lett., vol. 44, No. 2, pp. 415–419, Received Oct. 2, 1990.

M. Kotora et al., Journal of Molecular Catalysis, vol. 77, pp. 51–60, Received Jan. 3, 1992.

E.N. Zil'berman et al., Journal of Org. Chem. USSR, vol. 3, pp. 2101–2105, Dec., 1967.

*Primary Examiner*—Alan Siegel
*Attorney, Agent, or Firm*—Evenson, McKeown, Edwards & Lenahan, P.L.L.C.

[57] ABSTRACT

The present invention relates to a method for producing 1,1,1,3,3-pentafluoropropane. This method includes a step of adding hydrogen fluoride to 1,3,3,3-tetrafluoropropene in a liquid phase in the presence of a hydrohalogenation catalyst. This method is a useful method for producing 1,1,1,3,3-pentafluoropropane in an industrial scale, because yield of 1,1,1,3,3-pentafluoropropane is high. According to the invention, 1,3,3,3-tetrafluoropropene may be produced by a method including a step of reacting 1,1,1,3,3-pentachloropropane with hydrogen fluoride in a gas phase in the presence of a fluorination catalyst, or by another method including a step of reacting 1-chloro-3,3,3-trifluoropropene with hydrogen fluoride in a gas phase in the presence of a fluorination catalyst. According to the invention, 1-chloro-3,3,3-trifluoropropene may be produced by a method including a step of reacting 1,1,1,3,3-pentachloropropane with hydrogen fluoride in a gas phase in the presence of a fluorination catalyst.

22 Claims, No Drawings

METHOD FOR PRODUCING 1,1,1,3,3,-PENTAFLUOROPROPANE

BACKGROUND OF THE INVENTION

This invention relates to a method for producing 1,1,1,3,3-pentafluoropropane, which is useful as a foaming agent for foaming substances such as polyurethane, a refrigerant, and the like.

There are several conventional methods for producing 1,1,1,3,3-pentafluoropropane. For example, JP-A-Hei-6-256235 discloses a method for producing 1,1,1,3,3-pentafluoropropane from $CF_3$-CClX-$CF_2$Cl where X is hydrogen or chlorine, by catalytic hydrogenation. A preferable catalyst for this method is a common hydrogenation catalyst. U.S. Pat. No. 2,942,036 discloses a method of hydrogenating 1,2,2-trichloropentafluoropropane to produce 1,1,1,3,3-pentafluoropropane or 1,1,3,3,3-pentafluoro-1-propene or mixtures thereof. A catalyst for this method is palladium carried on activated carbon. These two methods mentioned hereinabove are superior in conversion and selectivity. However, these catalysts deteriorate considerably in these methods. Furthermore, it is necessary to prepare the raw material(s) of these methods in advance. Thus, these methods may not be suitable for the production of 1,1,1,3,3-pentafluoropropane in an industrial scale.

There is disclosed, in published English translation (pp. 1312–1317) of Izvestiya Akademii Nauk SSSR, Otdelenie Khimicheskikh Nauk, No. 8, pp. 1412–1418, August, 1960 (CA 55, 349f), a method for producing 1,1,1,3,3-pentafluoropropane by hydrogenating 1,1,3,3,3-pentafluoro-1-propene in the presence of Pd-$Al_2O_3$. However, it is difficult to find the raw material of this method (i.e., 1,1,3,3,3-pentafluoro-1-propene) on the market.

There is another method for producing 1,1,1,3,3-pentafluoropropane, comprising a step of fluorinating 1,1,1,3,3-pentachloropropane by hydrogen fluoride in the presence of a fluorination catalyst (see WO96/01797 and JP-A-Hei-8-104655). However, this method is relatively low in yield.

There is still another method for producing 1,1,1,3,3-pentafluoropropane, comprising a step of fluorinating 1,2,2-trihydrodichlorotrifluoropropane by hydrogen fluoride in the presence of a fluorination catalyst (see JP-A-Hei-8-73385). It is, however, necessary to prepare a raw material, 1,2,2-trihydrodichlorotrifluoropropane, of this method in advance.

Unlike 1,1,1,3,3-pentafluoropropane mentioned hereinabove, there is known another compound, 1,3,3,3-tetrafluoropropene, which is useful as an intermediate of medicines, of agricultural chemicals, and of functional materials, and as a refrigerant and the like. This compound is obtained, for example, by the following first and second processes. In the first process, 1,3,3,3-tetrafluoro-1-iodopropane is dehydroiodinated by alcoholic potassium hydroxide to produce 1,3,3,3-tetrafluoropropene (see R. N. Haszeldine et al., J. Chem. Soc.. 1953, 1199–1206; CA 48 5787f). In the second process, 1,1,1,3,3-pentafluoropropane is dehydrofluorinated by potassium hydroxide in dibutyl ether (see I. L. Knunyants et al., Izvest. Akad. Nauk S. S. S. R., Otdel. Khim. Nauk. 1960, 1412–1418; CA 55, 349f). These processes are superior in conversion and selectivity. According to these processes, however, it is necessary to use more than stoichiometric amount of potassium hydroxide and to prepare the raw materials (i.e., 1,3,3,3-tetrafluoro-1-iodopropane and 1,1,1,3,3-pentafluoropropane) in advance. Therefore, these processes are not suitable for an industrial scale production.

Unlike 1,1,1,3,3-pentalfluoropropane and 1,3,3,3-tetrafluoropropene mentioned hereinabove, there is known still another compound, 1-chloro-3,3,3-trifluoropropene, which is useful as an intermediate of medicines, of agricultural chemicals, of functional materials, and of fluorohydrocarbons. This compound is obtained, for example, by the following first to fifth processes. In the first process, 1,1,1-trifluoropropane is chlorinated to obtain 1,1,1-trifluoro-3,3-dichloropropane, and then this compound is dehydrochlorinated by an alcoholic basic compound to produce 1-chloro-3,3,3-trifluoropropene (see J. Am. Chem. Soc., 1942, 64, 1158). In the second process, hydrogen chloride is added to 3,3,3-trifluoropropyne to produce 1-chloro-3,3,3-trifluoropropene (see J. Chem. Soc., 1952, 3490). The second process is superior in conversion and selectivity. However, it is difficult to obtain the raw material of the second process (i.e., 3,3,3-trifluoropropyne) on the market. In the third process, 3-chloro-1,1,1-trifluoro-3-iodopropane is dehydroiodinated by alcoholic potassium hydroxide to produce 1-chloro-3,3,3-trifluoropropene (see J. Chem. Soc., 1953, 1199). In the fourth process, 3-bromo-3-chloro-1,1,1-trifluoropropane is dehydrobrominated by an alcoholic potassium hydroxide (see R. N. Haszeldine, J. Chem. Soc., 1951, 2495). The third and fourth processes are superior in conversion and selectivity. However, according to these processes, there is needed more than stoichiometric amount of potassium hydroxide, and it is necessary to prepare the raw materials in advance. Thus, there are problems to apply these processes to an industrial scale production. In the fifth process, 1,3,3,3-tetrachloropropene is fluorinated by hydrogen fluoride in the presence of an antimony catalyst (see U.S. Pat. No. 2,787,646). In the fifth process, there are a problem that it is difficult to obtain the raw material of the reaction on the market, and another problem that the yield of 1-chloro-3,3,3-trifluoropropene is poor for the industrial scale production.

SUMMARY OF THE INVENTION

It is an object of the present invention to provide a method for producing 1,1,1,3,3-pentafluoropropane, which method is free of the above-mentioned drawbacks.

It is a specific object of the present invention to provide a method for producing 1,1,1,3,3-pentafluoropropane with a high yield.

It is another object of the present invention to provide a method for continuously producing 1,3,3,3-tetrafluoropropene from a raw material which can be obtained on the market or can relatively easily be produced by a conventional method.

According to a first aspect of the present invention, there is provided a first method for producing 1,1,1,3,3-pentafluoropropane, comprising a step of adding hydrogen fluoride to 1,3,3,3-tetrafluoropropene in a liquid phase in the presence of a hydrohalogenation catalyst. The first method of the present invention is a useful method for producing 1,1,1,3,3-pentafluoropropane in an industrial scale, because yield of this product is high.

According to a second aspect of the present invention, there is provided a second method for producing 1,3,3,3-tetrafluoropropene, comprising a step of reacting 1,1,1,3,3-pentachloropropane with hydrogen fluoride in a gas phase in the presence of a fluorination catalyst. The second method of the present invention is a useful method for producing 1,3,3,3-tetrafluoropropene in an industrial scale, because 1,3,3,3-tetrafluoropropene can continuously be produced from 1,1,1,3,3-pentachloropropane which can be obtained on the market or can relatively easily be produced by one of the after-mentioned conventional methods.

According to a third aspect of the present invention, there is provided a third method for producing 1,3,3,3-tetrafluoropropene, comprising a step of reacting 1-chloro-3,3,3-trifluoropropene with hydrogen fluoride in a gas phase in the presence of a fluorination catalyst. The third method of the present invention is a useful method for producing 1,3,3,3-tetrafluoropropene in an industrial scale, because 1,3,3,3-tetrafluoropropene can continuously be produced from 1-chloro-3,3,3-trifluoropropene which can be obtained on the market or can relatively easily be produced from a raw material that is obtainable in a large amount used for an industrial scale production.

According to the present invention, there is provided a fourth method for producing 1-chloro-3,3,3-trifluoropropene, which is a raw material of the third method. The fourth method comprises a step of reacting 1,1,1,3,3-pentachloropropane with hydrogen fluoride in a gas phase in the presence of a fluorination catalyst. As stated above, a raw material of the fourth method, 1,1,1,3,3-pentachloropropane, is easily obtained by one of the after-mentioned conventional methods. Furthermore, the fourth method is useful as an industrial-scale method for producing 1-chloro-3,3,3-trifluoropropene, because yield of 1-chloro-3,3,3-trifluoropropene is high.

According to the present invention, the first and second methods may be combined in order to produce 1,1,1,3,3-pentafluoropropane from 1,1,1,3,3-pentachloropropane, and the first and third methods may be combined in order to produce 1,1,1,3,3-pentafluoropropane from 1-chloro- 3,3,3-trifluoropropene, and the first, third and fourth methods may be combined in order to produce 1,1,1,3,3-pentafluoropropane from 1,1,1,3,3-pentachloropropane.

DESCRIPTION OF THE PREFERRED EMBODIMENTS

In accordance with the first aspect of the present invention, there will be described in detail the above-mentioned first method for producing 1,1,1,3,3-pentafluoropropane, as follows.

A hydrohalogenation catalyst used in the first method is preferably at least one metal halide selected from the group consisting of titanium halides, tin halides, bismuth halides, antimony halides, and molybdenum halides. Each of these metal halides is chloride, bromide, iodide or fluoride. In case that an antimony halide is used as the hydrohalogenation catalyst, antimony contained in this halide may have an oxidation number of either +3 or +5 by the following reason. An antimony(III) halide, which is in a non-activated condition, is easily oxidized to an antimony(V) halide, which is in an activated condition and is high in catalytic activity, by chlorine, bromine, iodine or fluorine. Therefore, an antimony halide that is introduced as the hydrohalogenation catalyst into the reaction system of the first method is not limited to an antimony(V) halide, but may be either of an antimony(III) halide and an antimony (V) halide. Examples of an antimony halide used as the hydrohalogenation catalyst are antimony pentachloride, antimony pentabromide, antimony pentaiodide, antimony pentafluoride, antimony trichloride, antimony tribromide, antimony triiodide, and antimony trifluoride. Of these, antimony pentachloride is the most preferable. Examples of an titanium halide used as the hydrohalogenation catalyst are titanium tetrachloride, titanium tetrabromide, titanium tetraiodide, and titanium tetrafluoride. Of these, aluminum trichloride is the most preferable. Examples of a tin halide used as the hydrohalogenation catalyst are tin tetrachloride, tin tetrabromide, tin tetraiodide, and tin tetrafluoride. Of these, tin tetrachloride is the most preferable Bismuth trichloride is the most preferable in examples of a bismuth halide used as the hydrohalogenation catalyst. Molybdenum pentachloride is the most preferable in examples of an molybdenum halide used as the hydrohalogenation catalyst.

In the first method, the step may be conducted by a continuous operation, a batch operation, or a half-batch operation in which only the reaction product is continuously removed from a reactor. Hereinafter, the description of the first method will be concerned mainly with a batch operation. If the first method is conducted by another operation, it is optional to modify the reaction condition(s) of a batch operation, which will be described hereinafter.

In the first method, the hydrohalogenation catalyst is in an amount preferably of from 0.1 to 20 moles and more preferably of from 1 to 10 moles, per 100 moles of 1,3,3,3-tetrafluoropropene. If it is less than 0.1 moles, both of conversion of 1,3,3,3-tetrafluoropropene and yield of 1,1,1,3,3-pentafluoropropane may become too low. If it is greater than 20 moles, the production of tarry substances made up of high-boiling-point compounds may increase too much.

In the first method, the reaction temperature is preferably from 0 to 150° C. and more preferably from 20 to 120° C. If the temperature is lower than 0° C., both of conversion of 1,3,3,3-tetrafluoropropene and yield of 1,1,1,3,3-pentafluoropropane may become too low. If the temperature is higher than 150° C., pressure of the reaction system may become too high. With this, it may become difficult to properly conduct the reaction.

In the first method, almost a stoichiometric amount of hydrogen fluoride is sufficient for the reaction. It is particularly preferable that hydrogen fluoride is in an amount of from 1 to 10 moles per mol of 1,3,3,3-tetrafluoropropene. If it is less than 1 mol, conversion of 1,3,3,3-tetrafluoropropene may not become sufficiently high. If it is greater than 10 moles, conversion of 1,3,3,3-tetrafluoropropene will not improve further. Furthermore, it is not economically advantageous in terms of the recovery of the unreacted hydrogen fluoride.

In the first method, pressure needed to conduct the reaction varies depending on the reaction temperature, and is not particularly limited as long as the reaction mixture is maintained in the form of liquid in the reactor. It is preferably from 1 to 20 kg/cm$^2$, more preferably from 1 to 15 kg/cm$^2$.

In the first method, it is preferable to purge water as much as possible from 1,3,3,3-tetrafluoropropene, hydrogen fluoride, a hydrohalogenation catalyst, and the reaction system.

In the first method, a solvent may be added to the reaction system in order to adjust the reaction and to suppress deterioration of the hydrohalogenation catalyst. Examples of this solvent are 1,4-bistrifluoromethylbenzene, 2,4-dichlorobenzotrifluoride, and 1,1,1,3,3-pentafluoropropane which is the aimed product.

When the hydrohalogenation catalyst of the first method has deteriorated or has been a metal halide containing a metal having a lower oxidation number, this catalyst can be easily activated to the activated condition where its metal has a desired oxidation number. This activation is conducted by introducing chlorine into the reaction system at a temperature of from 10 to 100° C., in the presence of a solvent such as 1,1,1,3,3-pentafluoropropane. Upon or after the introduction, stirring is conducted, if necessary. For the activation, chlorine is used in an amount of from 1 to 100 moles per mol of the hydrohalogenation catalyst. If the temperature is lower than 10° C., it takes too long time to achieve the activation. If it is higher than 100° C., the coexisting solvent such as 1,1,1,3,3-pentafluoropropane may be chlorinated.

A reactor used in the fist method is preferably made of a material such as Hastelloy, stainless steel, Monel metal or nickel, or a material lined with one of these metals, tetrafluoroethylene resin, chlorotrifluoroethylene resin, vinylidene fluoride resin or PFA resin.

In the first method, the obtained 1,1,1,3,3-pentafluoropropane may be purified by a conventional method for purifying reaction products obtained by the fluorination. In this purification, for example, 1,1,1,3,3-pentafluoropropane, together with the unreacted hydrogen fluoride, is discharged in the form of liquid or gas, from a reactor. Then, an excessive amount of hydrogen fluoride is removed from the discharge by the liquid phase separation or the like. Then, an acid component is removed therefrom using water or a basic solution. After that, the aimed 1,1,1,3,3-pentafluoropropane having a high purity is obtained by distillation.

In accordance with the second and third aspects of the present invention, there will be described in detail the second and third methods for producing 1,3,3,3-tetrafluoropropene, respectively. As stated above, the second method comprises a step of reacting 1,1,1,3,3-pentachloropropane with hydrogen fluoride in a gas phase in the presence of a fluorination catalyst, and the third method comprises a step of reacting 1-chloro-3,3,3-trifluoropropene with hydrogen fluoride in a gas phase in the presence of a fluorination catalyst. Furthermore, according to the present invention, there will be described in detail the fourth method for producing 1-chloro-3,3,3-trifluoropropene. As stated above, the fourth method comprises a step of reacting 1,1,1,3,3-pentachloropropane with hydrogen fluoride in a gas phase in the presence of a fluorination catalyst.

1,1,1,3,3-pentachloropropane, which is a raw material of the second and fourth methods of the invention, may be produced, for example, by the following conventional first, second, and third processes. In the first process, vinylidene chloride is reacted with chloroform in the presence of copper-amine catalyst (see M. Kotora et al. (1991) React. Kinet. Catal. Lett., Vol. 44, No. 2, pp. 415–419). In the second process, carbon tetrachloride is reacted with vinyl chloride in the presence of copper-amine catalyst (see M. Kotora et al. (1992) J. of Molecular Catalysis, Vol. 77, pp. 51–60). In the third process, carbon tetrachloride is reacted with vinyl chloride in an isopropanol solvent, in the presence of a ferrous chloride catalyst (see E. N. Zil'berman et al. (1967) J. of Org. Chem. USSR, Vol. 3, pp. 2101–2105).

In each of the second and third methods, the fluorination catalyst is preferably an activated carbon that optionally carries thereon at least one compound of at least one metal. This activated carbon is not limited to a particular type. The activated carbon may be prepared from a vegetable raw material such as wood, sawdust, charcoal, coconut husk coal, palm core coal, or raw ash; a coal such as peat, lignite, brown coal, bituminous coal, or anthracite; a petroleum raw material such as petroleum residue, sulfuric sludge, or oil carbon; or a synthetic resin raw material. The activated carbon may be selected from various commercial activated carbons. Examples of commercial activated carbons that are usable in each of the second and third methods are an activated carbon having a trade name of CALGON GRANULAR ACTIVATED CARBON CAL that is made of bituminous coal and made by TOYO CALGON CO. and a coconut husk coal made by Takeda Chemical Industries, Ltd. An activated carbon used in the second and third methods is generally in the form of granules. Its shape and size are not particularly limited, and may be decided depending on the reactor's size.

As stated above, an activated carbon used in each of the second and third methods optionally carries thereon at least one compound of at least one metal selected from the group consisting of aluminum, chromium, manganese, nickel, cobalt, and titanium. This at least one compound is selected from oxides, fluorides, chlorides, fluorochlorides, oxyfluorides, oxychlorides, oxyfluorochlorides, and the like.

A method for preparing a catalyst used in each of the second and third methods is not particularly limited. An activated carbon which is modified or not by hydrogen fluoride or a chlorofluorohydrocarbon is useful for the second and third methods. Moreover, the activated carbon may be treated by immersion or spraying with a solution in which the at least one compound of the at least one metal is dissolved. Examples of a solvent of this solution are water, ethanol and acetone. Examples of the at least one compound to be dissolved into this solvent are nitrates, chlorides, and oxides of the at least one metal, such as chromium nitrate, chromium trichloride, chromium trioxide, potassium dichromate, titanium trichloride, manganese nitrate, manganese chloride, manganese dioxide, nickel nitrate, nickel chloride, cobalt nitrate, and cobalt chloride. The amount of the at least one metal that is carried on an activated carbon is preferably from 0.1 to 80 wt %, more preferably from 1 to 40 wt %, based on the total weight of the activated carbon.

The fluorination catalyst used in the fourth method has a first preferable example that is at least one compound of at least one metal selected from the group consisting of aluminum, chromium, manganese, nickel, and cobalt. Hereinafter, this example will be referred to as the first fluorination catalyst. Examples of the at least one compound of the first fluorination catalyst are oxide, fluoride, chloride, fluorochloride, oxyfluoride, oxychloride, and oxyfluorochloride. The at least one compound may be carried on a carrier such as an aluminum compound or activated carbon. Examples of this aluminum compound are aluminum oxide, fluoride, chloride, fluorochloride, oxyfluoride, oxychloride, and oxyfluorochloride.

In the fourth method, the manner of preparing the first fluorination catalyst is not particularly limited. When the at least one compound is not carried on a carrier, the at least one compound may be prepared, as follows. At first, a metal hydroxide is precipitated from a solution of a compound of the at least one metal, using a basic substance. After that, this metal hydroxide is turned into a metal oxide, and then this metal oxide is partially or completely modified by halogen, using hydrogen fluoride, hydrogen chloride, chlorofluorohydrocarbon, and the like. In contrast, when the at least one compound is carried on a carrier, the carrier may be immersed into a solution of the at least one compound, or alternatively this solution may be sprayed on the carrier. The carrier may be, for example, an aluminum oxide such as γ-alumina or an alumina that has previously been modified by hydrogen fluoride, hydrogen chloride, chlorofluorohydrocarbon or the like.

In the fourth method, the amount of the at least one metal of the first fluorination catalyst is preferably from 0.1 to 20 wt % and more preferably from 1 to 10 wt %, based on the total weight of the carrier. It is optional to add an additive that is at least one element of alkali-earth metals such as Mg and Ca and lanthanide series elements such as La and Ce, to the first fluorination catalyst. This additive prevents recrystallization of an oxyhalide used as the at least one metal or as the carrier, thereby maintaining activity of the first fluorination catalyst. Weight ratio of the at least one metal to the additive is preferably from 50:50 to 99.9:0.1 and more preferably from 70:30 to 99:1.

In the fourth method, at least one metal compound used for preparing the first fluorination catalyst may be at least one of nitrate, chloride, oxide and the like of the at least one metal, which is soluble in a solvent such as water, ethanol, or acetone. Examples of the at least one metal compound are chromium nitrate, chromium trichloride, chromium trioxide, potassium dichromate, manganese nitrate, manganese chloride, manganese dioxide, nickel nitrate, nickel chloride, cobalt nitrate, and cobalt chloride.

In the fourth method, the fluorination catalyst has further second and third preferable examples that are respectively a partially fluorinated aluminum oxide and a stainless steel that has been treated with hydrogen fluoride. Hereinafter, these preferable examples will respectively be referred to as the second and third fluorination catalysts. Aluminum oxide has various morphologies depending on the manner of preparing the same. Aluminum oxide used in the fourth method is not limited to a particular type, and γ-alumina can easily be found on the market and thus is preferably used for that. Of γ-alumina, there is preferably used in the fourth method an activated alumina that is generally used for supporting catalyst, that is relatively large in specific surface area, and that is superior in heat resistance. Examples of stainless steel used in the fourth method are ferrite-type stainless steel (SUS 304) and austenite-type stainless steels (SUS 304, 304L, 316, and 316L). Preferable examples of the same are stainless steels that are in the forms of wool, net, wire and thin tube, and a distillation tower's filler that is prepared from one of these stainless steels into an arbitrary shape.

In the fourth method, the manner of preparing the second and third fluorination catalysts is not particularly limited. The second fluorination catalyst may be prepared by sequential steps of (a) preparing aluminum oxide from the precursor in the form of sphere or rod; and (b) treating the aluminum oxide with a fluorine-containing compound by spraying of a hydrofluoric acid solution, by immersion into this solution, or by bringing the aluminum oxide into contact with a gas that is hydrogen fluoride, fluorohydrocarbon or chlorofluorohydrocarbon under an elevated temperature. The third fluorination catalyst is prepared by immersing stainless steel into a hydrofluoric acid solution, followed by drying, or by filling a reaction tube with stainless steel and then allowing hydrogen fluoride to flow through the reaction tube.

In each of the second, third and fourth methods, ratio by mol of 1,1,1,3,3-pentachloropropane or 1-chloro-3,3,3-trifluoropropene to hydrogen fluoride varies depending on the reaction temperature. In the second method, this ratio is preferably from 1/30 to 1/4 and more preferably from 1/10 to 1/4. In the third method, this ratio is preferably from 1/60 to 1/1 and more preferably from 1/30 to 1/1. In the fourth method, this ratio is preferably from 1/30 to 1/3, more preferably from 1/10 to 1/3. It is preferable to use more than the stoichiometric amount of hydrogen fluoride in the fluorination. Thus, the unreacted hydrogen fluoride may be separated from the unreacted organic matter and the reaction product by a conventional method, and then may be reused. Even if the amount of hydrogen fluoride is too much or too little, that is not critical to the fluorination of large scale, because low-fluorinated compounds, unreacted substances, and/or hydrogen fluoride, which usually accompanies the reaction product, is separated from the reaction product and is reused. But if the amount of hydrogen fluoride is too much, the amount of the reaction product contained in the unit volume of the gas released from the reactor may become too small. Furthermore, it may become difficult to separate the reaction product from a mixture of the reaction products and the unreacted hydrogen fluoride released from the reactor. If the amount of hydrogen fluoride is too small, conversion may become low, thereby lowering yield of the reaction product.

In each of the second, third and fourth methods, compositional change of the fluorination catalyst during the fluorination can effectively be prevented by treating, prior to the fluorination, the fluorination catalyst with a fluorination agent such as hydrogen fluoride, fluorohydrocarbon or fluorochlorohydrocarbon, at a temperature not lower than the reaction temperature of the fluorination. The fluorination catalyst can effectively be prolonged in lifetime, and furthermore conversion and yield of the fluorination can effectively be improved, by supplying the reactor with oxygen, chlorine, fluorohydrocarbon or fluorochlorohydrocarbon, during the fluorination.

In each of the second and third methods, the reaction temperature is preferably from 200 to 600° C. and more preferably from 300 to 500° C. In the fourth method, when the first fluorination catalyst is used, the reaction temperature is preferably from 100 to 450° C. and more preferably from 150 to 300° C. In this method, when either of the second and third fluorination catalysts is used, the reaction temperature is preferably from 200 to 500° C. and more preferably from 250 to 400° C. In each of the second, third and fourth methods, if the reaction temperature is too low, the reaction rate may become impractically slow. In each of these methods, if the reaction temperature is too high, the reaction rate becomes high. With this, however, the fluorination catalyst may become short in lifetime. Furthermore, there may be produced the decomposition products, excessively fluorinated products, and the like. Thus, selectivity of 1,3,3,3-tetrafluoropropene and 1-chloro-3,3,3-trifluoropropene may respectively be lowered in the second and third methods and the fourth method.

In each of the second, third and fourth methods, the reaction pressure is not particularly limited. It is preferably from 1 to 10 kg/cm$^2$ from the viewpoint of the selection of the reactor's material. It is preferable to select a reaction condition in which a hydrocarbon used as a raw material (i.e., 1,1,1,3,3-pentachloropropane or 1-chloro-3,3,3-trifluoropropene), intermediate products and hydrogen fluoride, which exist in the reaction system, are not liquefied in the reaction system. The contact time of the fluorination between the hydrocarbon and hydrogen fluoride is preferably from 0.1 to 300 seconds. In each of the second and third methods, it is more preferably from 5 to 60 seconds. In the fourth method, when the first fluorination catalyst is used, it is more preferably from 5 to 100 seconds; and, when either of the second and third fluorination catalysts is used, it is more preferably from 5 to 60 seconds.

The reactor's material used in each of the second, third and fourth methods is not particularly limited, as long as the reactor has a sufficient heat resistance and a sufficient corrosion resistance against hydrogen fluoride, hydrogen chloride and the like. It is preferably stainless steel, Hastelloy, Monel metal or platinum, or a material lined with one of these metals.

In each of the second, third and fourth methods, the reaction products may be purified by a conventional purification process that is not particularly limited. In this process, for example, the reaction products are washed with water and/or a basic solution to remove add substances such as hydrogen chloride and hydrogen fluoride. Then, the washed reaction products are dried and then distilled to remove organic impurities.

The first aspect of the present invention will be illustrated with reference to the following nonlimitative Examples 1–5.

EXAMPLE 1

In this example, 1,1,1,3,3-pentafluoropropane was prepared from 1,3,3,3-tetrafluoropropene, as follows, in accordance with the first method of the present invention.

At first, 6.0 g (0.02 mol) of antimony pentachloride (hydrohalogenation catalyst) and 100 g (5.0 mol) of hydrogen fluoride were introduced into a 500 ml autoclave made of stainless steel (SUS 316L) and equipped with a stirrer, a pressure regulating valve and a reflux condenser maintained at −30° C. This mixture in the autoclave was stirred for 30 minutes, thereby to activate the catalyst. After that, hydrogen fluoride, which had been generated by mixing antimony pentachloride and hydrogen fluoride, was discharged from the pressure regulating valve, thereby to reduce the inside pressure to atmospheric pressure. Then, the valve was closed, and then the autoclave was cooled down by dry ice and methanol. After that, 114 g (1.0 mol) of 1,3,3,3-tetrafluoropropene was introduced into the autoclave, and then autoclave's temperature was increased to 50° C., while the reaction mixture was stirred. 3.5 hr after the beginning of the reaction, the autoclave's temperature was decreased to room temperature. After that, a gas component of the autoclave was discharged therefrom by reducing the pressure to atmospheric pressure, then was allowed to flow through a water layer and then a concentrated sulfuric acid layer, and then was collected by a trap that was previously cooled down by dry ice and methanol. With this, 123 g of an organic matter was collected. With an analysis by gas chromatography, it was found that this organic matter contains 98.5% of 1,1,1,3,3-pentafluoropropane, 0.4% of 1,3,3,3-tetrafluoropropene, and 0.1% of 1-chloro-3,3,3-trifluoropropene.

EXAMPLES 2–5

In these examples, Example 1 was repeated except in that the type and amount of the hydrohalogenation catalyst were changed as shown in Table 1. The results are also shown in Table 1.

TABLE 1

| | Catalyst Type and Its Amount | Collected Organic Matter (g) | Selectivity of 1,1,1,3,3-pentafluoropropane (%) |
|---|---|---|---|
| Example 1 | $SbCl_5$ (6 g) | 123 | 98 |
| Example 2 | $SnCl_4$ (5 g) | 110 | 41 |
| Example 3 | $BiCl_5$ (6 g) | 108 | 35 |
| Example 4 | $TiCl_4$ (4 g) | 105 | 85 |
| Example 5 | $MoCl_5$ (5 g) | 102 | 67 |

The second aspect of the present invention will be illustrated with reference to the following nonlimitative Examples 6–9.

EXAMPLE 6

In this example, 1,3,3,3-tetrafluoropropene was prepared from 1,1,1,3,3-pentachloropropane, as follows, in accordance with the second method of the present invention.

The fluorination catalyst was prepared as follows. At first, 100 g of an activated carbon (PCB 4×10 meshes) that is prepared from a crashed coconut husk made by TOYO CALGON CO. was immersed into 150 g of pure water. Separately, a solution was prepared by dissolving 40 g of $CrCl_3.6H_2O$ into 100 g of pure water. This solution was mixed with the mixture of activated carbon and pure water, and the resultant mixture was allowed to stand still for one day and one night. Then, the activated carbon was separated from the mixture by filtration, and then was baked at 200° C. for 2 hr in an electric furnace. The thus obtained activated carbon carrying thereon chromium was put into a cylindrical reaction tube that is equipped with an electric furnace and made of stainless steel (SUS316L) and that has a diameter of 5 cm and an axial length of 30 cm. Then, the reaction tube temperature was increased to 200° C., while nitrogen gas was allowed to flow through the reaction tube. Then, at the time when water flow from the reaction tube has stopped, it was started to allow hydrogen fluoride to flow therethrough, together with the nitrogen gas, and then the hydrogen fluoride concentration was gradually increased. When a hot spot produced by the adsorption of hydrogen fluoride on the chromium-carried activated carbon reached the end of exit of the reaction tube, the reaction tube temperature was further increased to 400° C. Then, this condition was maintained for 2 hr, thereby preparing the fluorination catalyst.

Then, the fluorination was conducted as follows. At first, a cylindrical reaction tube for conducting a gas phase reaction was charged with 150 cc of the above-prepared fluorination catalyst. This reaction tube was equipped with an electric furnace and was made of stainless steel (SUS316L) and had a diameter of 1 inch and an axial length of 30 cm. The reaction tube temperature was increased to 200° C., while nitrogen gas was allowed to flow therethrough at a flow rate of about 100 cc/min, Then, hydrogen fluoride gas was allowed to flow therethrough at a flow rate of about 0.10 g/min, together with nitrogen gas. Under this condition, the reaction tube temperature was increased to a temperature of 500° C. and then was maintained at this temperature for 1 hr. Then, the reaction tube temperature was lowered to 400° C., and then the reaction (fluorination) was started by supplying the reaction tube with 1,1,1,3,3-pentachloropropane that had previously been vaporized, at a flow rate of 0.32 g/min, and with hydrogen fluoride at a flow rate of 0.10 g/min, as shown in Table 2. 1 hr after the start of the reaction, the reaction became stable. After that, the reaction products (gas) released from the reaction tube were bubbled for 2 hr into water to remove an acid gas therefrom and then were collected by a trap cooled down in dry ice and acetone. With this, 21.2 g of an organic matter was obtained. This organic matter was analyzed with a gas chromatograph, and the results of this analysis are shown in Table 3.

In each of this example, the after-mentioned Examples 7–12, Referential Examples 1–2 and Examples 17–26, the rest of the organic matter, except 1,3,3,3-tetrafluoropropene, 1,1,1,3,3-pentafluoropropane, and 1-chloro-3,3,3-trifluoropropene which are mentioned in Tables 3, 5 and 9, was an unidentified substance(s), and each amount of 1-chloro-3,3,3-trifluoropropene and 1,3,3,3-tetrafluoropropene, which is shown in Tables 3, 5 and 9, is the total amount of cis- and trans-isomers thereof.

TABLE 2

| | Reaction Temp. (° C.) | Reactants Flow Rates (g/min) | |
|---|---|---|---|
| | | 1,1,1,3,3-pentachloropropane | Hydrogen Fluoride |
| Example 6 | 400 | 0.32 | 0.10 |
| Example 7 | 400 | 0.16 | 0.20 |
| Example 8 | 400 | 0.15 | 0.21 |
| Example 9 | 500 | 0.15 | 0.21 |
| Ref. Ex. 1 | 400 | 0.32 | 0.10 |

TABLE 3

| | Reaction Products Weight (g) | Chemical Composition of Reaction Products (mol %) | | |
|---|---|---|---|---|
| | | 1,3,3,3-tetra-fluoropropene | 1,1,1,3,3-penta-fluoropropane | 1-chloro-3,3,3-trifluoro-propene |
| Example 6 | 21.2 | 28.8 | 7.4 | 63.1 |
| Example 7 | 10.7 | 18.4 | 0.6 | 79.6 |
| Example 8 | 10.3 | 9.3 | 1.0 | 67.5 |
| Example 9 | 9.3 | 10.5 | 2.3 | 69.0 |
| Ref. Ex. 1 | 21.9 | 0.9 | 8.0 | 90.6 |

EXAMPLE 7

In this example, Example 6 was repeated except in that 200 g of a 20% TiCl₃ aqueous solution was used in place of 140 g of the CrCl₃ aqueous solution in the preparation of the fluorination catalyst, and that the reaction (fluorination) conditions were modified as shown in Table 2.

EXAMPLES 8–9

In these examples, Example 6 was repeated except in that an activated carbon itself, which does not carry thereon any metal, was used as the fluorination catalyst in place of the chromium-carried activated carbon, and that the reaction (fluorination) conditions were modified as shown in Table 2.

REFERENTIAL EXAMPLE 1

In this referential example, Example 6 was repeated except in that the preparation of the fluorination catalyst was modified as follows, That is, a chromium-carried aluminum was used as the fluorination catalyst in this referential example.

At first, 1 liter of a CrCl₃ aqueous solution was prepared by dissolving 336 g of CrCl₃.6H₂O into pure water. Into this solution, 250 cc of an activated alumina in-the form of sphere that is made by SUMITOMO CHEMICAL CO., LTD. and has a trade name of NKH3-24, a diameter of from 2 to 4 mm, a specific surface area of 340 m²/g and a morphological property of γ-alumina was immersed, and then this solution was allowed to stand still for one day and one night. After that, the activated alumina was separated from the solution by filtration, and then was dried for one day and one night at 100° C. in a hot-air circulating type oven. The thus obtained chromium-carried alumina was put into a cylindrical reaction tube that is equipped with an electric furnace and is made of stainless steel (SUS316L) and has a diameter of 5 cm and an axial length of 30 cm. The reaction tube temperature was increased to 300° C., while nitrogen gas was allowed to flow therethrough. Then, at the time when it was found that steam flow therefrom stopped, it was started to allow hydrogen fluoride to flow therethrough, together with nitrogen gas. Then, hydrogen fluoride concentration of the mixture of hydrogen fluoride and nitrogen was gradually increased. When a hot spot produced by fluorinating the chromium-carried alumina reached the end of exit of the reaction tube, the reaction tube temperature was further increased to 450° C. Then, this condition was maintained for 1 hr, thereby preparing the fluorination catalyst.

EXAMPLE 10

In this example, Example 6 was repeated except in that the flow rate of hydrogen fluoride during the fluorination was 0.15 g/min, in place of 0.10 g/min, and that 1-chloro-3,3,3-trifluoropropene that had previously been vaporized, in place of 1,1,1,3,3-pentachloropropane, was allowed to flow through the reaction tube at a flow rate of 0.06 g/min, as shown in Table 4. With this, 6.0 g of an organic matter was collected. The results of gas chromatographic analysis of this organic matter are shown in Table 5.

TABLE 4

| | Reaction Temp. (° C.) | Reactants Flow Rates (g/min) | |
|---|---|---|---|
| | | 1-chloro-3,3,3-trifluoropropene | Hydrogen Fluoride |
| Example 10 | 400 | 0.06 | 0.15 |
| Example 11 | 400 | 0.04 | 0.18 |
| Example 12 | 500 | 0.14 | 0.14 |
| Ref. Ex. 2 | 400 | 0.06 | 0.15 |

TABLE 5

| | Reaction Products Weight (g) | Chemical Composition of Reaction Products (mol %) | | |
|---|---|---|---|---|
| | | 1,3,3,3-tetra-fluoropropene | 1,1,1,3,3-penta-fluoropropane | 1-chloro-3,3,3-trifluoro-propene |
| Example 10 | 6.0 | 73.0 | 11.7 | 14.1 |
| Example 11 | 4.0 | 28.1 | 0.8 | 71.1 |
| Example 12 | 13.2 | 22.3 | 0.5 | 71.0 |
| Ref. Ex. 2 | 6.6 | 0.3 | 20.8 | 77.0 |

EXAMPLE 11

In this example, Example 10 was repeated except in that 200 g of a 20% TiCl₃ aqueous solution was used in place of 140 g of the CrCl₃ aqueous solution in the preparation of the fluorination catalyst, and that the reaction (fluorination) conditions were modified as shown in Table 4.

EXAMPLES 12

In this example, Example 10 was repeated except in that an activated carbon itself, which does not carry thereon any metal, was used as the fluorination catalyst in place of the chromium-carried activated carbon, and that the reaction (fluorination) conditions were modified as shown in Table 4.

REFERENTIAL EXAMPLE 2

In this referential example, Example 10 was repeated except in that the fluorination catalyst was prepared in a manner that is the same as that of Referential Example 1.

EXAMPLES 13

In this example, 1-chloro-3,3,3-trifluoropropene was produced by fluorinating 1,1,1,3,3-pentachloropropane with hydrogen fluoride in a gas phase in the presence of the first fluorination catalyst, as follows.

The first fluorination catalyst was prepared in the same manner as that of Referential Example 1, except in that the reaction tube temperature was increased to and maintained for 1 hr at 350° C., in place of 450° C.

Then, the fluorination was conducted as follows. At first, 50 cc of the above-prepared first fluorination catalyst was put into a cylindrical reaction tube that is the same as that of Example 6. Then, the reaction tube temperature was increased to 300° C., while nitrogen gas was allowed to flow therethrough at a flow rate of about 190 cc/min. Then, hydrogen fluoride gas was also allowed to flow therethrough at a flow rate of about 0.25 g /min, together with nitrogen gas. Then, the reaction tube temperature was increased to 350° C., and then this condition was maintained for 1 hr. Then, the reaction tube temperature was decreased to 220° C., and then the reaction (fluorination) was started by supplying the reaction tube with 1,1,1,3,3-pentachloropropane that had previously been vaporized, at a flow rate of 0.35 g/min, and with hydrogen fluoride at a flow rate of 0.29 g/min, as shown in Table 6. 1 hr after the start of the reaction, the reaction became stationary. After that, the reaction products were collected in a manner that is similar to that of Example 6. The thus obtained organic matter was analyzed with a gas chromatograph, and the results of this analysis are shown in Table 7.

TABLE 6

|  | Reaction Temp. (° C.) | Reactants Flow Rates (g/min) | |
| --- | --- | --- | --- |
|  |  | 1,1,1,3,3-pentachloropropane | Hydrogen Fluoride |
| Example 13 | 200 | 0.35 | 0.29 |
| Example 14 | 200 | 0.30 | 0.25 |
| Example 15 | 150 | 0.27 | 0.24 |
| Example 16 | 300 | 0.28 | 0.27 |

TABLE 7

|  | Nitrogen Gas Flow Rate (ml/min) | Yield of 1-chloro-3,3,3-trifluoropropene (%) | Purity of 1-chloro-3,3,3-trifluoropropene (%) |
| --- | --- | --- | --- |
| Example 13 | 190 | 95 | 97 |
| Example 14 | 170 | 86 | 97 |
| Example 15 | 185 | 82 | 86 |
| Example 16 | 185 | 84 | 84 |

EXAMPLES 14–16

In these examples, Example 13 was repeated except in that the reaction conditions were modified as shown in Tables 6–7.

EXAMPLE 17

In this example, 1-chloro-3,3,3-trifluoropropene was produced by reacting 1,1,1,3,3-pentachloropropane with hydrogen fluoride in a gas phase in the presence of the second fluorination catalyst, as follows.

The second fluorination catalyst was prepared as follows. At first, 300 g of the activated alumina having a trade name of NKH3-24 was washed with water to remove a powder attached to the surface of the activated alumina. Separately, 10% hydrofluoric acid solution was prepared by dissolving 115 g of anhydrous hydrogen fluoride into 1,035 g of water. Then, the hydrofluoric acid solution was gradually poured on the activated alumina. After stirring, this mixture was allowed to stand still for 3 hr. After that, the activated alumina separated from the solution was washed with water, then was separated from water by filtration, and then was dried at 200° C. for 2 hr in an electric furnace. Then, 150 cc of the dried activated alumina was put into a stainless steel reaction tube having an inner diameter of 1 inch and an axial length of 30 cm. Then, this reaction tube was put into the electric furnace, and then the electric furnace temperature was increased to 200° C., while nitrogen gas was allowed to flow through the reaction tube. After that, hydrogen fluoride gas together with nitrogen gas was allowed to flow therethrough to treat the activated alumina with hydrogen fluoride As this treatment proceeded, the temperature of catalyst increased. In this treatment, flow rates of nitrogen and hydrogen fluoride were respectively adjusted such that the temperature of catalyst did not exceed 400° C. After this exothermic reaction of the activated alumina with hydrogen fluoride has finished, the reaction tube was further kept in the electric furnace at 400° C. for 2 hr.

Then, a cylindrical reaction tube for conducting a gas phase reaction was charged with 150 cc of the above-treated activated alumina. This reaction tube was equipped with an electric furnace and was made of stainless steel (SUS316L) and had a diameter of 1 inch and an axial length of 30 cm. The reaction tube temperature was increased to 300° C., while nitrogen gas was allowed to flow therethrough at a flow rate of about 160 cc/min. After the temperature rose to 300° C., hydrogen fluoride gas was allowed to flow therethrough at a flow rate of about 0.20 g/min, together with nitrogen gas. Under this condition, the reaction tube temperature was increased to a maximum temperature of 350° C. and then was maintained at this temperature for 1 hr. Then, the reaction tube temperature was lowered to 250° C., and then the reaction (fluorination) was started by supplying the reaction tube with 1,1,1,3,3-pentachloropropane that had previously been vaporized, at a flow rate of 0.27 g/min, as shown in Table 8. One hour after the start of the reaction, the reaction became stable. After that, the reaction products (gas) released from the reaction tube were bubbled into water to remove an acid gas therefrom and then were collected by a trap cooled in dry ice and acetone. With this, 17.8 g of an organic matter was obtained. This organic is matter was analyzed with a gas chromatograph, and the results of this analysis are shown in Table 9.

TABLE 8

|  | Reaction Temp. (° C.) | Reactants Flow Rates (g/min) | |
| --- | --- | --- | --- |
|  |  | 1,1,1,3,3-pentachloropropane | Hydrogen Fluoride |
| Example 17 | 250 | 0.27 | 0.20 |
| Example 18 | 250 | 0.56 | 0.19 |
| Example 19 | 300 | 0.56 | 0.19 |
| Example 20 | 350 | 0.56 | 0.19 |
| Example 21 | 400 | 0.56 | 0.19 |
| Example 22 | 250 | 1.01 | 0.40 |
| Example 23 | 300 | 1.01 | 0.40 |
| Example 24 | 250 | 1.01 | 0.40 |
| Example 25 | 300 | 1.01 | 0.40 |
| Example 26 | 350 | 1.01 | 0.40 |

TABLE 9

| | Reaction Products Weight (g) | Chemical Composition of Reaction Products (mol %) | | |
|---|---|---|---|---|
| | | 1,3,3,3-tetra-fluoropropene | 1,1,1,3,3-penta-fluoropropane | 1-chloro-3,3,3-trifluoro-propene |
| Example 17 | 17.8 | 1.2 | 0.9 | 96.1 |
| Example 18 | 38.0 | 0.2 | 0.1 | 97.3 |
| Example 19 | 37.4 | 1.0 | 0.4 | 96.7 |
| Example 20 | 37.7 | 1.0 | 0.2 | 96.7 |
| Example 21 | 36.1 | 1.5 | 0.3 | 94.2 |
| Example 22 | 67.2 | 0.4 | 0.1 | 87.2 |
| Example 23 | 66.4 | 0.8 | 0.2 | 97.2 |
| Example 24 | 66.2 | 0.5 | 0.3 | 97.2 |
| Example 25 | 65.4 | 0.9 | 0.2 | 97.5 |
| Example 26 | 64.4 | 1.2 | 0.6 | 96.2 |

EXAMPLES 18–21

In these examples, Example 17 was repeated except in that the reaction conditions were modified as shown in Table 8. Only in Example 21, however, the reaction tube temperature was increased to a maximum of 400° C., in place of 350° C.

EXAMPLES 22–23

In these examples, Example 17 was repeated except in that the reaction conditions were modified as shown in Table 8 and that the nitrogen gas flow rate was modified into 320 cc/min.

EXAMPLE 24

In this example, 1-chloro-3,3,3-trifluoropropene was produced by fluorinating 1,1,1,3,3-pentachloropropane with hydrogen fluoride in a gas phase in the presence of the third fluorination catalyst, as follows. -

The third fluorination catalyst was prepared as follows. At first, 150 cc of pole rings each having a diameter of 5 mm and an axial length of 6 mm, which are used for a distillation tower and are made of stainless steel (SUS316L), was put into a stainless steel reaction tube having an inner diameter of 1 inch and an axial length of 30 cm. Then, this reaction tube was put into the electric furnace, and the electric furnace temperature was increased to 200° C., while nitrogen gas was allowed to flow through the reaction tube. After that, hydrogen fluoride gas together with nitrogen gas was allowed to flow therethrough to treat the pole rings with hydrogen fluoride. In this treatment, flow rates of nitrogen and hydrogen fluoride were respectively adjusted for 2 hr such that the furnace temperature did not exceed 400° C. With this, the third fluorination catalyst was prepared.

Then, a cylindrical reaction tube that is the same as that of Example 17 was charged with 150 cc of the above-prepared third fluorination catalyst. The reaction tube temperature was increased to 300° C., while nitrogen gas was allowed to flow therethrough at a flow rate of about 320 cc/min. Then, hydrogen fluoride gas was allowed to flow therethrough at a flow rate of about 0.40 g/min, together with nitrogen gas. Under this condition, the reaction tube temperature was increased to a maximum temperature of 350° C. and then was maintained at this temperature for 1 hr. Then, the reaction tube temperature was lowered to 250° C., and then the reaction (fluorination) was started by supplying the reaction tube with hydrogen fluoride at a flow rate of 0.40 g/min and with 1,1,1,3,3-pentachloropropane that had previously been vaporized, at a flow rate of 1.01 g/min, as shown in Table 8. 1 hr after the start of the reaction, the reaction became stable. After that, the reaction products were collected in a manner that is the same as that of Example 17. With this, 66.2 g of an organic matter was obtained. This organic matter was analyzed with a gas chromatograph, and the results of this analysis are shown in Table 9.

EXAMPLES 25–26

In these examples, Example 24 was repeated except in that the reaction temperature was modified as shown in Table 8.

What is claimed is:

1. A method for producing 1,1,1,3,3-pentafluoropropane, comprising a step of adding hydrogen fluoride to 1,3,3,3-tetrafluoropropene in a liquid phase in the presence of a hydrohalogenation catalyst that comprises at least one antimony halide; wherein said 1,3,3,3-tetrafluoropropene is produced by reacting 1,1,1,3,3-pentachloropropane with hydrogen fluoride in a gas phase in the presence of a fluorination catalyst at a temperature of 400–500° C.

2. A method according to claim 1, wherein said at least one antimony halide is selected from the group consisting of antimony pentachloride, antimony pentabromide, antimony pentaiodide, antimony pentafluoride, antimony trichloride, antimony tribromide, antimony triiodide, and antimony trifluoride.

3. A method according to claim 1, wherein said hydrohalogenation catalyst is antimony pentachloride.

4. A method according to claim 1, wherein said hydrohalogenation catalyst is present in an amount of from 0.1 to 20 moles per 100 moles of 1,3,3,3-tetrafluoropropene.

5. A method according to claim 1, wherein said adding step is conducted at a temperature of from 0 to 150° C.

6. A method for producing 1,3,3,3-tetrafluoropropene, comprising a step of reacting 1,1,1,3,3-pentachloropropane with hydrogen fluoride in a gas phase in the presence of a fluorination catalyst at a temperature of 400–500° C.

7. A method according to claim 6, wherein said fluorination catalyst is an activated carbon.

8. A method according to claim 7, wherein said activated carbon carries thereon at least one compound of at least one metal selected from the group consisting of aluminum, chromium, manganese, nickel, cobalt, and titanium.

9. A method according to claim 8, wherein said at least one compound is selected from the group consisting of oxides, fluorides, chlorides, fluorochlorides, oxyfluorides, oxychlorides, and oxyfluorochlorides.

10. A method according to claim 8, wherein said at least one metal is in an amount of from 0.1 to 80 wt %, based on the total weight of said activated carbon.

11. A method according to claim 6, wherein, prior to said step, the fluorination catalyst is treated with a fluorine-containing compound at a temperature that is not lower than a reaction temperature of said step.

12. A method for producing 1,3,3,3-tetrafluoropropene, comprising:

reacting 1,1,1,3,3-pentachloropropane with hydrogen fluoride in a gas phase in the presence of a fluorination catalyst at a temperature of 150–400° C. to produce 1-chloro-3,3,3-trifluoropropene; and reacting said 1-chloro-3,3,3-trifluoropropene with hydrogen fluoride in a gas phase in the presence of a fluorination catalyst.

13. A method according to claim 12, wherein said fluorination catalyst is one of a fluorinated aluminum oxide and a fluorinated stainless steel.

14. A method according to claim 13, wherein said fluorination catalyst is a fluorinated aluminum oxide.

15. A method according to claim 13, wherein said fluorination catalyst is a fluorinated stainless steel.

16. A method according to claim 12, wherein said fluorination catalyst is at least one compound of at least one metal selected from the group consisting of aluminum, chromium, manganese, nickel, and cobalt.

17. A method according to claim 16, wherein said at least one compound is selected from the group consisting of oxides, fluorides, chlorides, fluorochlorides, oxyfluorides, oxychlorides, and oxyfluorochlorides.

18. A method according to claim 16, wherein said at least one compound is carried on a carrier.

19. A method according to claim 18, wherein said carrier is at least one selected from the group consisting of aluminum oxides, aluminum fluorides, aluminum chlorides, aluminum fluorochlorides, aluminum oxyfluorides, aluminum oxychlorides, aluminum oxyfluorochlorides, and activated carbon.

20. A method according to claim 16, wherein the step is conducted at a temperature of from 100 to 450° C.

21. A method according to claim 12, wherein, prior to the step, the fluorination catalyst is treated with a fluorine-containing compound at a temperature that is not lower than a reaction temperature of the step.

22. A method according to claim 21, wherein said fluorine-containing compound is at least one compound selected from the group consisting of hydrogen fluoride, fluorohydrocarbons, and fluorochlorohydrocarbons.

* * * * *